United States Patent [19]

van der Burgt et al.

[11] 4,038,629
[45] July 26, 1977

[54] PROPAGATION DELAY METER

[75] Inventors: Cornelis Martinus van der Burgt; Gerardus Andreas van Maanen, both of Eindhoven, Netherlands

[73] Assignee: U.S. Philips Corporation, New York, N.Y.

[21] Appl. No.: 574,349

[22] Filed: May 5, 1975

[30] Foreign Application Priority Data

May 6, 1974 Netherlands .................. 7406033

[51] Int. Cl.² ............................................. G01S 9/66
[52] U.S. Cl. ............................ 340/3 E; 73/560; 340/5 S; 340/8 FT
[58] Field of Search .............. 181/33 E, 175; 350/292, 350/293, 294; 73/560; 340/5 S, 3 E, 8 FT; 310/9.1

[56] References Cited

U.S. PATENT DOCUMENTS

| 2,778,273 | 1/1957 | Fellmeth ........................... 350/293 |
| 3,184,959 | 5/1965 | Suellentrop et al. ............ 340/5 S X |
| 3,273,111 | 9/1966 | Parenti ............................. 340/5 S |

Primary Examiner—Richard A. Farley
Attorney, Agent, or Firm—Frank R. Trifari; Bernard Franzblau

[57] ABSTRACT

For accurate measurements of the sound velocity in liquids, for example water, the propagation delay is measured between an ultrasonic wave which is emitted by a transducer and the wave which returns to the transducer upon reflection. By making the reflector spherical and disposing it at a distance from the transducer which is within 1½ times the length of the Fresnel region of the emitted acoustic wave, a favorable ratio between the 1 τ and the 2 τ signal is obtained, which ratio can be further improved when the central portion of the reflector is slightly flattened.

10 Claims, 7 Drawing Figures

PROPAGATION DELAY METER

The invention relates to an apparatus for measuring the propagation delay between an acoustic wave emitted by a transducer and the wave reflected by a reflector. In this context the terms "acoustic" and "sound" respectively are used in the wider sense, covering also the non-audible, generally ultrasonic vibrations. The invention is specifically intended for measuring the velocity of sound gradient in water, for example in the sea, in order to collect information about the variation of sound paths in the sea-water, from which, in turn, the presence or absence of irregularities in the ocean bottom or objects under the water can be derived. For a very "cheap" operational (i.e., one which can be used at the full speed of a ship) disposable meter for real-time measurement of the depth dependence of the velocity of sound in sea-water down to a depth of for example 500 to 2000 meters, the variations of the velocity of sound being real-time recorded on board ship with an accuracy which substantially equal that of the best known non-operational (only usable with an anchored ship) or laboratory instruments, in spite of the following very unfavorable factors which are inherent in the operational character of the rapidly sinking (at a rate of 5 to 6 m/s) very small disposable probe, allowance must be made for the following circumstances:

1. Strongly varying temperature and pressure to which the electronic and acoustical elements are subjected;
2. "Substantially" varying supply voltage of the built-in very small battery;
3. High flow rate of the seawater through the acoustic measuring cell;
4. Very small (for example 2 × 26 mm) acoustic measuring pathlength.

To date two arrangements are known in this field. One is a non-operational arrangement which measures the velocity of sound, by means of a large measuring instrument which is slowly lowered on a heavy cable from an anchored ship. A second one is an operational arrangement which does not measure the velocity of sound but instead measures the parameter temperature which, together with other parameters, (the known depth and unknown salinity) determines the velocity of sound.

Generally, the velocity of sound can be measured with the aid of a transducer which emits an acoustic wave train. This wave train is made to reflect against a reflector which is disposed at a fixed distance from the transducer, after which the reflected wave impinges on the transducer in which it produces an electric voltage with a time delay relative to the emitted wave, which is a measure of the velocity of sound to be measured. In this respect, it is of importance that the distance between the transducer and reflector does not vary with temperature, which may be achieved by a suitable choice of materials and design. Furthermore, it is essential in this respect that undesired reflected waves do not reach the transducer. For this the transducer is, amongst other things, provided with a suitable backing. Finally, it is necessary that the wave which returns to the transducer after being reflected once be distinguished optimally (electronically) from further disturbing waves, for example, from the wave which returns to the transducer after having travelled to and fro twice. In respect of the last-mentioned requirement the invention affords a marked improvement and is characterized in that the reflector has a surface which is spherical towards the transducer and is disposed at a distance from the transducer which is smaller than 1½ times the length of the Fresnel region of the acoustic wave which is emitted by the transducer, but greater than ½ times said Fresnel region. The length of the Fresnel region is defined in this respect in accordance with the text by J. Matauschek, Introduction To Ultrasonic Technique 1962, pages 50 and 51.

The invention will be described with reference to the drawing, in which.

Figure 1:
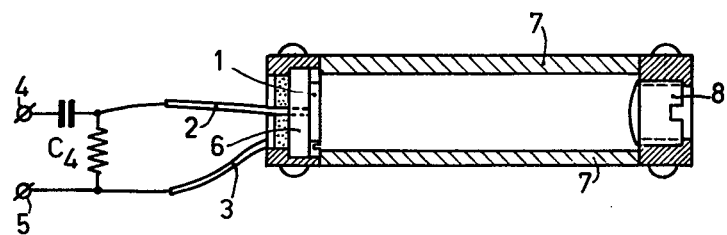
FIG. 1 shows an apparatus according to the invention.

The apparatus of FIG. 1 comprises a transducer 1 which, via connecting leads 2 and 3, is connected to input terminals 4 and 5. At the rear the transducer is provided with a backing 6 and together with said backing it is accommodated in a housing 7, which at its other end carries a reflector 8. At the long sides the housing 7 is open so that the water can freely flow into the space between the transducer 1 and the reflector 8. The housing is made of a material with a low coefficient of thermal expansion. Moreover, the fixing material for securing the transducer 1 and the reflector 8 has been selected so that the distance between the transducer 1 and reflector 8 does not vary with temperature.

To the terminals 4–5 an electrical pulse is applied of a duration which substantially equals half a period of the natural oscillation of the transducer 1. As a result, the transducer is excited and emits an acoustic vibration which after some oscillations assumes its maximum amplitude and subsequently decreases. The acoustic vibration propagates through the medium in the housing 7 — in particular seawater — and is reflected against the reflector 8 and after a time $\tau$ it reaches the transducer 1 again.

Figure 2:
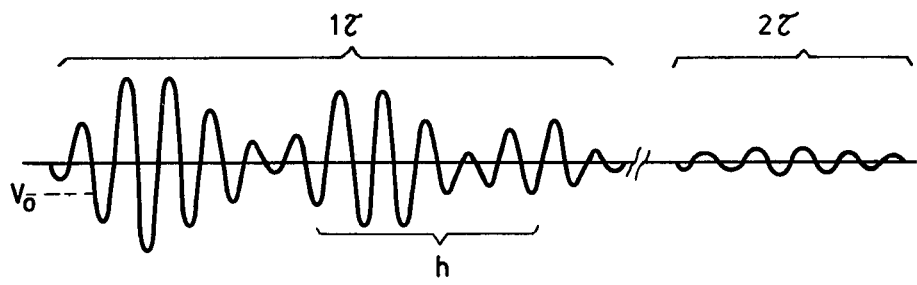
FIG. 2 represents the wave pattern of the returning wave at the transducer as a function of time.

FIG. 2 shows the variation of said vibration as a function of time. It appears that the amplitude of the third half sinewave is sufficiently greater than, for example more than 15 dB, the amplitude of the first half sinewave so that the corresponding voltage is capable of actuating an electrical circuit with a threshold voltage $V_o$. This is initially followed by a gradual decay of the oscillation and subsequently a slightly attenuated repetition $h$ of the first-mentioned oscillatory effect. This is caused by the backing 6 in which the acoustic vibration propagates backwards, subsequently reflects against the left rear wall and then reaches the transducer 1 with some delay relative to the previously discussed oscillation.

Figure 3:
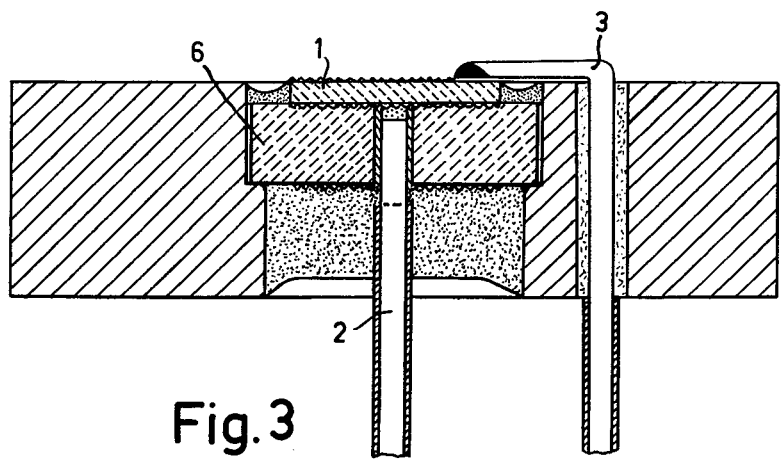
FIG. 3 shows an embodiment of the transducer section.

For the backing the same material is selected as for the transducer 1, for example a lead titanate-zirconate. The usual remanent polarization of said electric material may be dispensed with in the case of the backing. The dimensions of the backing member and the transducer body have been selected so as to differ substantially, as can be seen in FIG. 3. For the transducer 1, a thin circular disc is selected within a thickness which approximately equals half the wavelength of the acoustic wave. The backing has a slightly greater diameter and a substantially, i.e., a few times, greater thickness. Owing to the choice of the same material the acoustic matching at the interface of the transducer 1 and the backing 6 is perfect so that no undesired reflection of the acoustic vibration can occur at said interface. However, the wave which propagates backwards from the transducer (to the bottom), in total traverses a path which is twice the thickness of the backing 6 longer than the wave which is radiated directly in the forward direction. The said repetition $h$ of the first oscillation phenomenon therefore no longer disturbs the accurate detection of the reflected wave, wherefore the backing at the same time may serve for a correct mounting of the transducer 1, as is shown in FIG. 3.

Nearly a time $\tau$ after the wave phenomenon shown at the left of FIG. 2 has reached the transducer 1, the so-called $2\tau$ reflection signal — shown at the right of FIG. 2 — is received. This signal is produced as a result of the wave which is emitted in the forward direction after reflection at the reflector 8, reflection at the transducer 1 and once again reflecting off of the reflector 8 and thereby reaching the transducer 1 again. Although said $2\tau$ signal is substantially weaker than the $1\tau$ signal, it may give rise to undesired errors. Said $2\tau$ signal may have a disturbing effect on the $1\tau$ signal derived from an electrical pulse which is applied to the terminals at a time $\tau$ after the electrical signal from which said $2\tau$ signal is derived.

Figure 4:
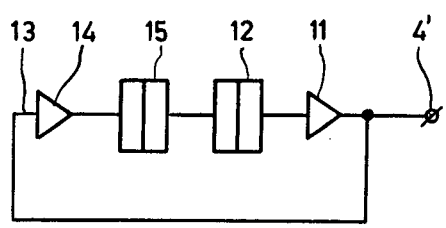
FIG. 4 is the circuit diagram of a pulse generator for the transducer.

Said electrical pulse is supplied by the output amplifier 11 of the generator circuit of FIG. 4. The amplifier 11 is controlled by a highly asymmetrical multivibrator circuit 12 which produces a pulse whose duration substantially equals half the period of the natural oscillation of the transducer 1, while the repetition time of said pulses in the freely oscillating condition is slightly longer than the maximum time to be measured $\tau$. The output terminal 4' of said generator circuit is connected to one of the input terminals (for example 4) of the apparatus of FIG. 1, while the other input terminal (5) is grounded. The $1\tau$ signal which returns to the transducer 1 will produce an electrical voltage which, via the terminal 4', reaches the input 13 of the generator circuit of FIG. 4. In this circuit said voltage is amplified in an amplifier 14 and subsequently applied to a monostable multivibrator circuit (for example a Schmitt trigger) 15, which has a trigger level corresponding to the voltage $V_o$ (FIG. 2) and which, after triggering, assumes its original state within a time which is smaller than the smallest time to be measured $\tau$.

Upon arrival of the $1\tau$ reflection signal at the transducer 1 the corresponding voltage will exceed the trigger level $V_o$. As a result the monostable multivibrator 5 is triggered, which in its turn causes the astable multivibrator 12 to produce a pulse, which pulse, after amplification in amplifier 11 is fed, via terminals 4' and 4, to the transducer 1 as an electrical drive pulse. Although said pulse also appears at terminal 13, this will have no further consequences because the monostable MV 15 has not yet then returned to its original — triggerable — state. Thus, a pulse train appears whose repetition time is accurately related to the time $\tau$ to be measured. Said pulses can be transmitted to a central station, for example the research vessel, via a long thin cable.

Figure 5:
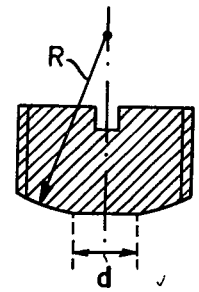
FIG. 5 shows an embodiment of the reflector section.

FIG. 5 shows the reflector enlarged. The side (at the bottom in FIG. 5) which faces the transducer 1 (FIG. 1) is spherical with a flattened central portion. The distance between the reflector 8 and the transducer 1 is smaller than $1\frac{1}{2}$ times the Fresnel region of the acoustic wave which is transmitted by the transducer 1, but greater than $\frac{1}{2}$ times said Fresnel region. As is known, the average energy density over the cross-sectional area of the housing 7 is virtually constant within the Fresnel region. At a greater distance, viz greater than $1\frac{1}{2}$ times the length of the Fresnel region, it passes into the Fraunhofer region, the energy being partly radiated laterally and on an average decreasing substantially inside the housing 7. Said effect is employed to improve the ratio between the $1\tau$ and the $2\tau$ reflection signals.

The substantially plane acoustic wave, which originates from the transducer 1, impinges completely onto the reflector 8 as there is not yet any lateral loss of energy. At the reflector 8 said wave is reflected with a slight divergence owing to the convex shape of said reflector, which entails a slight loss of the (useful) $1\tau$ signal which is incident on the transducer 1. Said loss decreases if the reflector exhibits a flattened portion as described hereinafter. The wave which is incident on the transducer 1 is now again reflected in the direction of the reflector 8, but it has now traversed such a long path that it is situated in the Fraunhofer region where there is a substantial lateral energy dispersion. Said dispersion is substantially emphasized by the convex shape of the reflector 8 so that only a small portion of the energy hits the transducer 1 as a $2\tau$ signal. However, as in the case of a spherical reflector, the absolute magnitudes of both the $1\tau$ and the $2\tau$ signal also decrease, so that the detection accuracy with which the detection threshold $V_c$ is passed may be affected, wherefor a certain compromise is to be made as regards the radius of curvature of the reflector, which on the one hand is correlated with the diameter of the transducer and on the other hand is also dependent on the reflector material.

Figure 6:
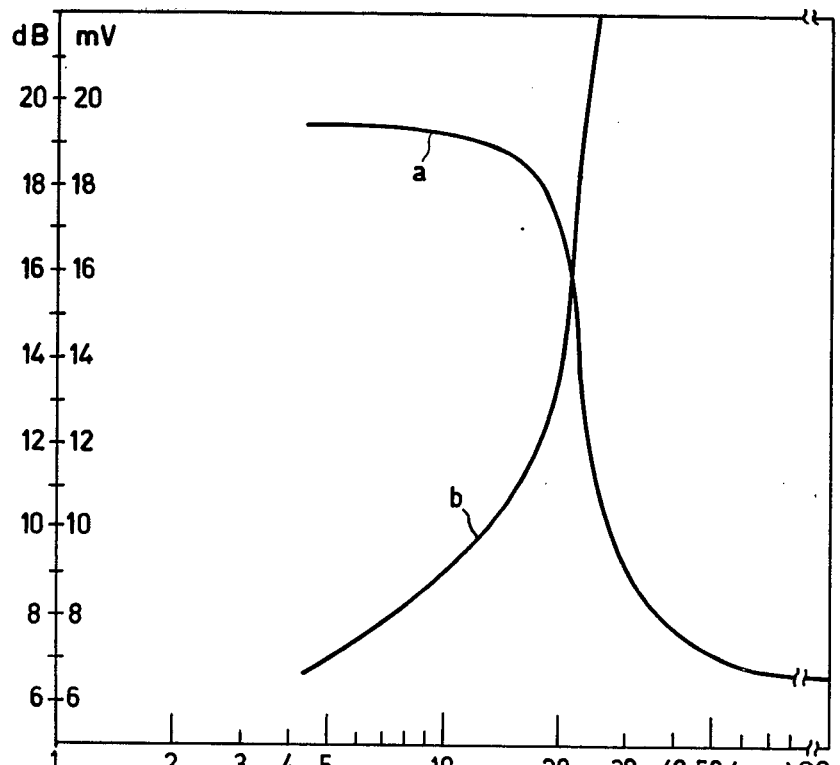
FIGS. 6 and 7 show graphs which demonstrate the effect of the invention.

FIG. 6 illustrates the general behavior. For small values of the radius of curvature R a very good ratio of the $1\tau$ signal to the $2\tau$ signal is found (curve $a$), but the absolute magnitude of the $1\tau$ signal decreased to an inacceptably small value (curve $b$). For a metal (for example brass) reflector a good compromise for R lies between 3 and 6 times the diameter D of the transducer 1, whereas for a plastic (for example "perspex") reflector it is between 6 and 12 times the said diameter.

Figure 7:
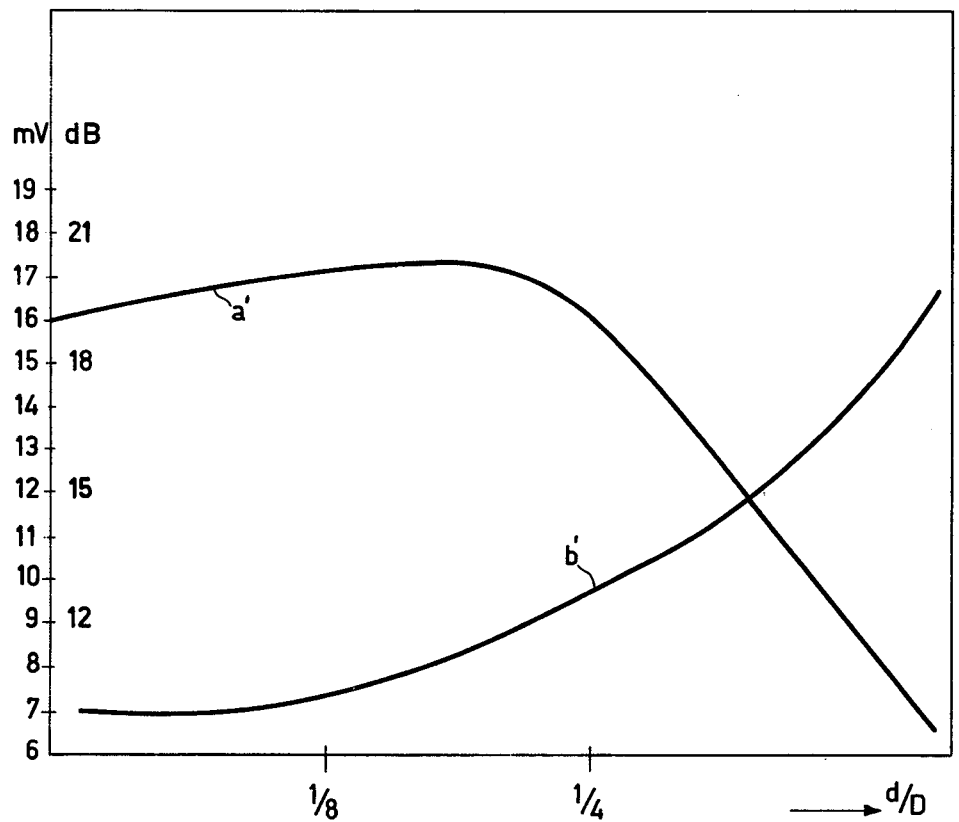

For a completely flat reflector (R = infinity) a very unfavorable ratio of the $1\tau$ to the $2\tau$ signal would be found (right part of curve $a$ in FIG. 6). In spite of this, partial flattening of the reflector, as is demonstrated in FIG. 6, yields an appreciable improvement. FIG. 7 illustrates the influences of said flattening for an optimum choice of the radius of curvature R. The diameter $d$ of the flattened portion in relation to the transducer diameter D is plotted horizontally, the $1\tau$ to $2\tau$ ratio (curve $a'$) and the strength of the $1\tau$ signal (curve $b'$) respectively being plotted vertically. In the range between approx. $\frac{1}{8}$ and $\frac{1}{4}$ times the diameter of the transducer there is hardly any change or even a slight improvement of the $1\tau$–$2\tau$ ratio (curve $a'$), but a very substantial increase of the $1\tau$ signal itself (curve $b'$).

What is claimed is:

1. Apparatus for measuring the propagation delay of an acoustic wave in a fluid medium comprising, a transducer for launching an acoustic wave along a given path in the fluid medium, a reflector of acoustic energy positioned in the fluid medium in the path of said acoustic wave at a distance from the transducer which is less than $\frac{1}{2}$ times the length of the Fresnel region of the acoustic wave launched by the transducer and greater than one half times said Fresnel region, said reflector having a convex surface facing the transducer for reflecting the launched acoustic wave back towards the transducer, and means coupled to the transducer and responsive to an acoustic wave reflected back from the reflector for deriving an electric control signal.

2. An apparatus as claimed in claim 1, characterized in that the reflector comprises a plastic material and the curved surface of the reflector has a radius of curvature between 6 and 12 times the diameter of the transducer and that said curved surface has a flattened central portion with a diameter between $\frac{1}{8}$ and $\frac{1}{4}$ the transducer diameter.

3. An apparatus as claimed in claim 1 wherein said control signal deriving means includes an electric pulse generator having a given threshhold value, and means connecting the transducer to the electrical pulse generator which, upon receipt of a reflected wave at the transducer which exceeds said threshold value, generates a new drive pulse for the transducer.

4. An apparatus as claimed in claim 1 further comprising a backing member made of the same material as the transducer and with a slightly greater diameter and a substantially greater thickness than that of the transducer, said transducer being mounted on the backing member.

5. An apparatus as claimed in claim 1 wherein the radius of curvature of the reflector curved surface is between three and six times the diameter of the transducer and said curved surface includes a flat central portion with a diameter between $\frac{1}{8}$ and $\frac{1}{4}$ the transducer diameter.

6. An apparatus as claimed in claim 1 wherein said control signal deriving means includes an electric pulse generator having a given voltage threshold level, and means connecting the transducer to the electric pulse generator which responds to a reflected wave received at the transducer and exceeding said threshold level to generate a drive pulse for the transducer.

7. An apparatus as claimed in claim 1 wherein the radius of curvature of the reflector curved surface is at least three times the diameter of the transducer and said curved surface includes a flat central reflecting area.

8. An apparatus as claimed in claim 7 wherein said transducer comprises a thin circular disc having a thickness dimension approximately half the wavelength of the acoustic wave, and further comprising a backing member supporting the disc and made of the same material as the disc, said backing member being thicker than the disc and of a greater diameter than said disc.

9. An apparatus as claimed in claim 8 further comprising an elongate housing in which the transducer and reflector are mounted at opposite ends thereof, said housing having openings in the longitudinally extending wall for the passage of the fluid medium.

10. An apparatus as claimed in claim 7 wherein said control signal deriving means includes an electric pulse generator having a given voltage threshold level and coupled to the transducer to generate a drive pulse for each reflected wave received at the transducer above the threshold level thereby producing a sequence of pulses whose repetition period is related to the propagation delay time between the transducer and reflector.

* * * * *

UNITED STATES PATENT AND TRADEMARK OFFICE
CERTIFICATE OF CORRECTION

PATENT NO. : 4,038,629
DATED : July 26, 1977
INVENTOR(S) : CORNELIS M. VAN DER BURGT ET AL It is certified that error appears in the above-identified patent and that said Letters Patent are hereby corrected as shown below:

Column 3, line 26, after "terminals" there should be --4-5--;

Signed and Sealed this

Fourth Day of July 1978

[SEAL]

Attest:

RUTH C. MASON
Attesting Officer

DONALD W. BANNER
Commissioner of Patents and Trademarks